United States Patent

Clemens et al.

[11] Patent Number: 5,395,337
[45] Date of Patent: Mar. 7, 1995

[54] NEEDLE RETRACTION SYSTEM

[76] Inventors: Anton H. Clemens, 5854 Schumann Dr., Madison, Wis. 53711; Victor M. Haughton, 1071 Waterville Rd., Oconomowoc, Wis. 53066

[21] Appl. No.: 114,472
[22] Filed: Aug. 31, 1993
[51] Int. Cl.⁶ ............................................... A61M 5/00
[52] U.S. Cl. ..................................... 604/110; 604/195
[58] Field of Search ............... 604/110, 195, 263, 218, 604/220

[56] References Cited

U.S. PATENT DOCUMENTS

| | | |
|---|---|---|
| 2,722,215 | 11/1955 | Dahlgren . |
| 2,841,143 | 7/1958 | Bertram . |
| 3,825,003 | 7/1974 | Kruck . |
| 4,009,716 | 3/1977 | Cohen . |
| 4,573,976 | 3/1986 | Sampson et al. . |
| 4,664,259 | 5/1987 | Landis . |
| 4,676,783 | 6/1987 | Jagger et al. . |
| 4,747,831 | 5/1988 | Kulli . |
| 4,767,413 | 8/1988 | Haber et al. . |
| 4,826,484 | 5/1989 | Haber et al. . |
| 4,838,869 | 6/1989 | Allard . |
| 4,874,382 | 10/1989 | Lindemann et al. . |
| 4,955,870 | 9/1990 | Ridderheim et al. . |
| 4,994,034 | 2/1991 | Botich et al. . |
| 5,000,736 | 3/1991 | Kaufhold, Jr. et al. . |
| 5,211,629 | 5/1993 | Pressly et al. ..................... 604/110 |

FOREIGN PATENT DOCUMENTS 9211883  7/1992  WIPO ................. 604/195

Primary Examiner—John D. Yasko
Attorney, Agent, or Firm—Andrus, Sceales, Starke & Sawall

[57] ABSTRACT

A retractable needle medical assembly includes a barrel and a plunger assembly defining an internal passageway within which a retraction member is mounted. The retraction member is biased into the passageway, by means of a spring or a vacuum located within the passageway. The medical assembly further includes a needle assembly consisting of a needle mounted to a hub. The hub is releasably engaged with the barrel. In one embodiment, an automatic retraction system is provided for engaging the retraction member with the hub upon movement of the plunger assembly toward the hub, and automatically releasing engagement between the hub and the barrel. Final movement of the plunger assembly toward the needle assembly disengages a retaining ring which retains the retraction member in position at the end of the passageway. The retraction member and needle assembly are then drawn into the passageway, to enclose the end of the needle to prevent accidental contact therewith and subsequent reuse of the medical assembly. The invention further contemplates a manual actuator system disposed between the needle hub and the barrel, for releasing engagement therebetween upon manual actuation by the user to result in withdrawal of the retraction member and needle into the passageway. The needle retraction system may be incorporated into a medical device such as a syringe, or into a blood collection system.

18 Claims, 5 Drawing Sheets

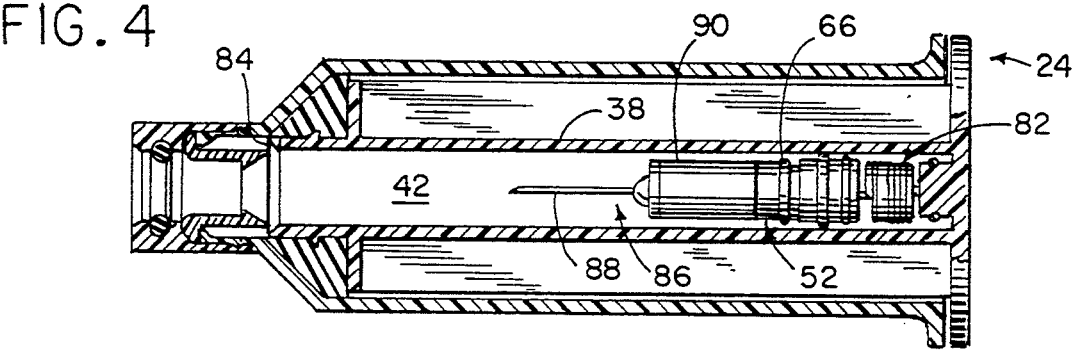
FIG. 4
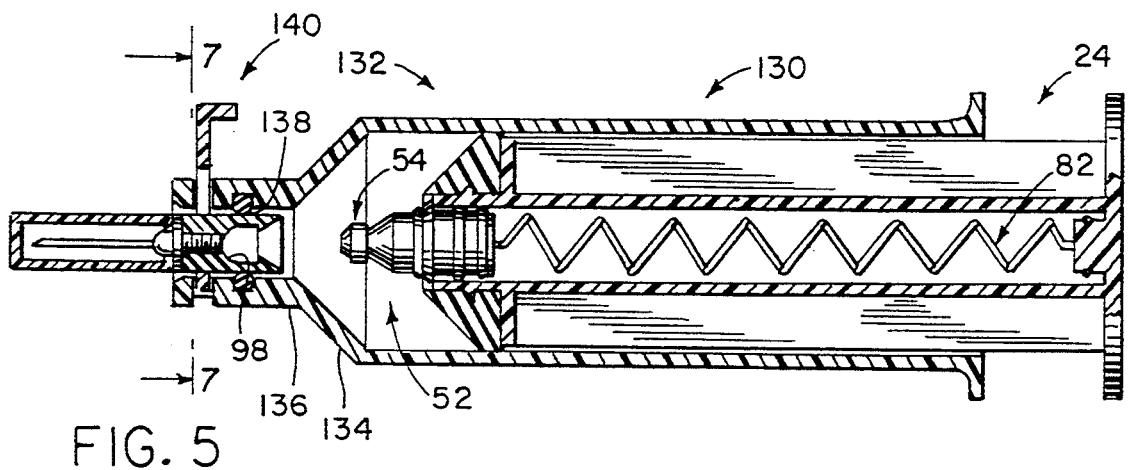
FIG. 5
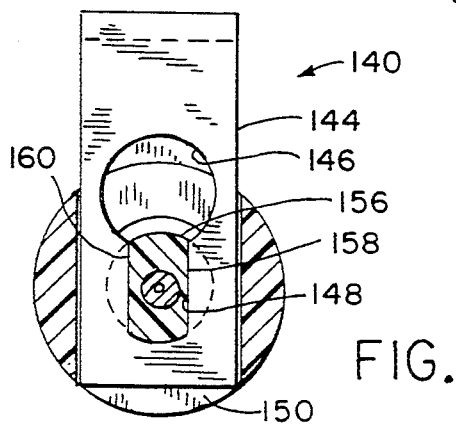
FIG. 6
FIG. 7

NEEDLE RETRACTION SYSTEM

BACKGROUND AND SUMMARY

This invention pertains to a syringe or the like for injecting or withdrawing a fluid into or from a patient, and more particularly to a needle retraction system for disarming such a device after use.

The hazards associated with accidental needle sticks are well known. Many issued patents disclose syringes or the like having mechanisms for retracting or otherwise enclosing a syringe needle after use, to prevent accidental contact with the needle.

It is an object of the present invention to provide an improved needle retraction mechanism for use with a syringe or the like for preventing accidental needle sticks. It is a further object of the invention to provide a needle retraction mechanism which is relatively simple in its construction and operation.

In accordance with one aspect of the invention, a syringe assembly includes a barrel having an internal cavity and defining a first closed end and a second open end. A plunger is mounted for longitudinal sliding movement within the barrel cavity. The plunger includes a longitudinal internal passageway. A first end of the plunger is disposed within the barrel cavity, and a second end of the plunger is disposed exteriorly of the barrel. The internal passageway opens onto the first end of the plunger. A retraction member is releasably engaged with the plunger, and is located within the internal passageway at the first end of the plunger. Bias means is provided for urging the retraction member into the passageway toward the second end of the plunger. In one form, the bias means consists of a spring interconnected between the retraction member and the plunger. A needle assembly consists of a needle engageable with a hub member, with the hub member including a passage establishing communication between the barrel cavity and the needle lumen. The needle is selectively engageable with the hub member such that the needle is engaged just prior to use of the syringe assembly. This enables the operator of the syringe assembly to select the appropriately sized needle according to the application in which the syringe assembly is used. In one form, the needle includes a head having external threads engageable with internal threads formed in the passage of the hub member. This enables the operator to remove the needle, if already in place, and replace it with a different needle if desired. In another form, the needle head includes a frustoconical cam surface defining a shoulder, and the hub passage is shaped so as to receive the frustoconical head of the needle. The hub member further includes resilient fingers having hooks at their forward ends, and the fingers are forced outwardly during insertion of the head into the needle passage. The fingers return to their original position to engage the shoulder defined by the needle head after placement of the needle head into the passage, so as to engage the needle with the hub member. In this arrangement, the needle cannot be selectively removed from the hub member after connection thereto.

In accordance with another aspect of the invention, engagement means may be interposed between the retraction member and the hub member for engaging the retraction member with the hub member upon movement of the plunger toward the first end of the barrel. A selectively actuable release mechanism maintains the retraction member in position within the plunger passageway at the first end of the plunger against the force of the bias means prior to engagement of the retraction member with the hub member during movement of the plunger toward the first end of the barrel. The release mechanism functions to release engagement of the retraction member with the plunger after engagement of the retraction member with the hub member. A releasable retainer mechanism is interposed between the hub member and the barrel for releasably engaging the hub member with the barrel. The releasable retainer mechanism is operable to release engagement between the barrel and the hub member, either before or after engagement of the retraction member with the hub member, to provide withdrawal of the hub member and needle into the passageway of the plunger after use of the syringe.

In accordance with yet another aspect of the invention, the plunger longitudinal internal passageway may be defined by a sleeve engaged with the closed end of the barrel. The sleeve includes a first end engaged with the closed end of the barrel and a second end spaced therefrom, preferably extending outwardly of the open end of the barrel. The hub member is disposed within the sleeve adjacent its first end, and bias means, such as in the form of a spring, is interposed between the hub member and the sleeve for biasing the hub member toward the second end of the sleeve. A releasable retainer mechanism is interposed between the hub member and the sleeve. The releasable retainer mechanism is movable between an engaged position in which the hub member is maintained in a fixed position adjacent the first end of the sleeve, and a disengaged release position. An actuator member is interconnected with the releasable retainer mechanism for selectively moving the releasable retainer mechanism to its release position in response to actuation by the operator to provide withdrawal of the hub member, and thereby the needle, into the sleeve to disarm the syringe assembly when desired. The actuator is located adjacent the open end of the barrel, and is engageable by the operator's thumb or finger so as to provide movement of the releasable retainer mechanism to its release position at any time during movement of the plunger. This enables the operator to disarm the syringe assembly whether or not all of the fluid has been ejected from the barrel. Once the hub member is moved to the second end of the sleeve by operation of the bias means, the bias means maintains the hub member in position therein to prevent subsequent reuse of the syringe assembly. Preferably, a one-way stop is provided in the sleeve to engage the hub member to prevent it from moving toward the first end of the sleeve after the hub member has passed by the stop member during disarming of the syringe assembly.

In accordance with further aspects of the invention, the hub member may be received within a sleeve which is engageable with the exterior of the barrel for engaging the hub member with the first end of the barrel. Further, the releasable retainer mechanism may be actuated automatically in response to movement of the plunger. In this form of the invention, the releasable retainer mechanism may take the form of a base disposed between the sleeve and the first end of the barrel, mounted to the barrel by engagement of the sleeve with the barrel. A series of flexible retaining fingers extend from the base and releasably engage the hub member. Movement of the plunger toward the first end of the barrel engages the retraction member with the fingers, which functions to flex the fingers outwardly to release engagement of the hub member with the barrel. Alternatively, the releasable retainer mechanism may take the form of a manually operated actuator member engaged between the barrel and the hub member, to retract the needle after use upon manual actuation by the user. The manually operated actuator member is movable between a retaining position and a release position, and functions to retain the hub member in position relative to the barrel when in its retaining position against the force of the biasing means when the retraction member is engaged with the hub member, and to release engagement of the hub member with the barrel when in its release position to allow the bias means to withdraw the retraction member, the hub member and the needle into the passageway. The first closed end of the barrel terminates in one or more walls defining a restricted passage within which the hub member is disposed when engaged with the barrel. The manually operated actuator member is engaged with the hub member, and is movably mounted to the one or more walls defining the restricted passage between its retaining position and its release position.

In either the manual or automatic versions summarized above, the bias means may take the form of a spring, as noted previously, or alternatively may be in the form of a vacuum provided in the passageway for urging the retraction member toward the second end of the passageway.

The selectively actuable release mechanism may be in the form of peripheral ridge structure provided on the retraction member, and a retaining ring interposed between the peripheral ridge structure and a peripheral end wall defined by the passageway at the first end of the plunger. Movement of the plunger toward the first end of the barrel results in the peripheral end wall forcing the retaining ring over the peripheral ridge structure, to release engagement of the retainer member with the plunger. In this manner, the retraction member functions to withdraw the hub member into the internal passageway defined by the plunger under the influence of the biasing means after the releasable retainer mechanism is operated to release engagement between the barrel and the hub member.

The invention further contemplates a method of disarming a syringe after use, substantially in accordance with the foregoing summary.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings:

FIG. 4 is a view similar to FIG. 1, showing the needle assembly withdrawn into the internal passageway of the plunger under the influence of the biasing means for disarming the syringe after use;

FIG. 5 is a view similar to FIG. 1, showing an alternative embodiment of the invention in which a manually operable actuator member retains the hub member of the needle assembly in engagement with the first end of the barrel;

FIG. 6 is an enlarged partial section view, similar to FIG. 2, showing the syringe assembly of FIG. 5 in a position in which the retraction member is engaged with the hub member of the needle assembly;

FIG. 7 is a section view taken along line 7—7 of FIG. 5;

DETAILED DESCRIPTION OF THE INVENTION

Figure 1:
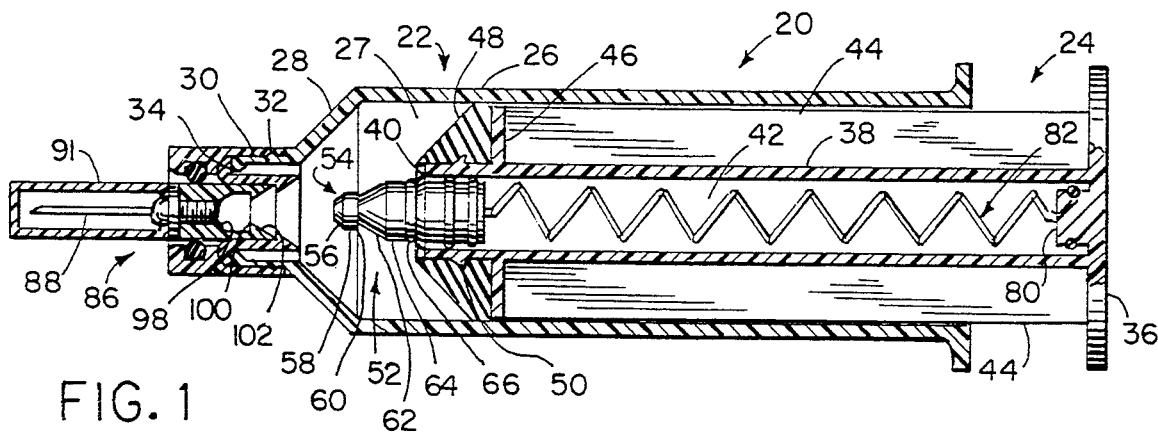
FIG. 1 is a longitudinal cross-sectional view of a syringe incorporating the needle retraction apparatus and method of the invention, showing the position of the plunger prior to engagement of the retraction member with the hub member during movement of the plunger toward the first end of the barrel.

FIG. 1 illustrates a syringe assembly 20 which generally includes a barrel 22 and a plunger 24. Barrel 22 includes a cylindrical side wall 26 defining an internal cavity 27, and a frustoconical wall 28 located between side wall 26 and a forwardly extending cylindrical end wall 30. End wall 30 includes a circumferential rib 32, and terminates in a forward end 34.

Plunger 24 includes a thumb plate 36 and a forwardly extending cylindrical wall 38 which terminates in a forward end 40. Cylindrical wall 38 defines an internal passageway 42. Ribs 44 extend outwardly from cylindrical wall 38, and extend between thumb plate 36 and a ring 46. A resilient plunger head 48 is mounted to the forward end of plunger 24. Head 48 defines a passage within which the end portion of cylindrical wall 38 is received. A groove is formed in the internal passageway of head 48, for receiving a peripheral rib 50 located toward the forward end of cylindrical wall 38. With this arrangement, head 48 is assembled onto plunger 24 by means of a rearward push-on motion, to engage the groove provided in the internal passage through head 48 with rib 50 and to abut the rearward surface of head 48 with the forward surface of ring 46, to retain head 48 in position on plunger 24. In a manner as is known, the outer peripheral edge of head 48 provides a fluid-tight seal with the inner surface of syringe wall 26.

Figure 2:
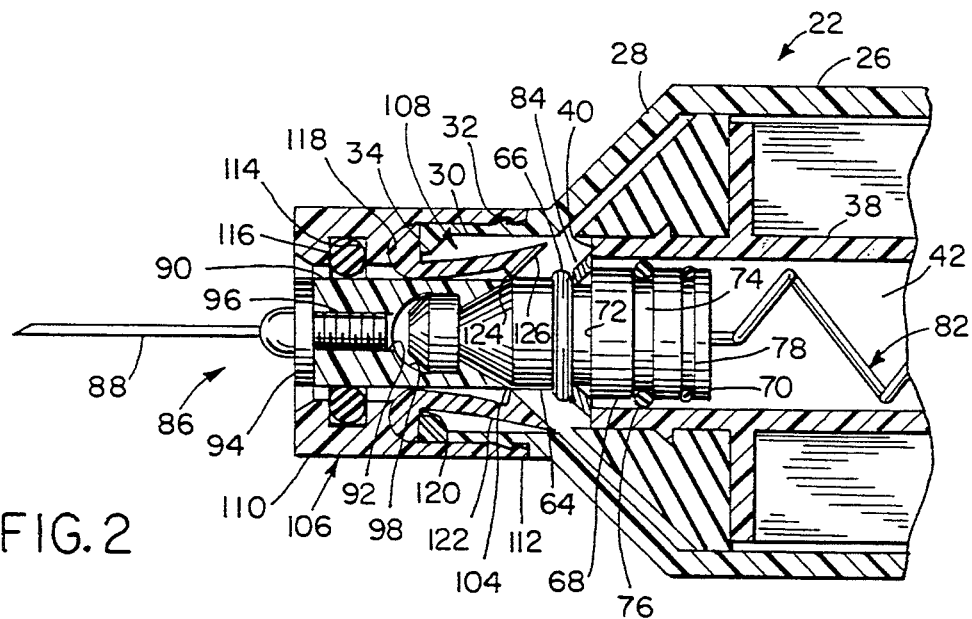
FIG. 2 is a partial longitudinal section view of the end portion of the syringe of FIG. 1, showing engagement of the retraction member with the hub member of the needle assembly.

A retraction member, shown generally at 52, is interconnected with plunger 24 at the forward end of cylindrical wall 38. The forward end of retraction member 52 defines a head 54 having an angled leading surface 56, a side surface 58 and a circumferential shoulder 60. Rearwardly of shoulder 60, head 52 defines an angled actuator surface 62 and a side surface 64. Side surface 64 is provided with peripheral ridge structure, in the form of a ring 66 engaged within a groove formed in side surface 64. Referring to FIG. 2, retraction member 52 rearwardly of side surface 64 defines an enlarged rear portion including a side wall 68, a rear end surface 70 and a shoulder 72 disposed between side surfaces 64 and 68. A groove 74 is formed in side surface 68, and an O-ring 76 is seated within groove 74 for providing a fluid-tight seal between plunger passageway 42 and internal cavity 27 defined by barrel 22. A groove 78 is formed in retraction member side wall 68 rearwardly of groove 74.

Referring to FIG. 1, a boss 80 is formed integrally with plunger thumb plate 36, extending forwardly into passageway 42. A spring 82 extends between boss 80 and retraction member 52. Spring 82 is connected at its rearward end to boss 80 by means of a groove formed in the side wall of boss 80. At its forward end, spring 82 is engaged within groove 78.

A retaining ring 84 is positioned between ring 66 and annular end surface 40 defined by cylindrical wall 38 of plunger 24. Retaining ring 84 is constructed so as to flare outwardly in a rearward direction, so that the forward end of ring 84 is closely engaged with retraction member 52 rearwardly of ring 66. Retaining ring 84 is thus substantially frustoconical in shape, and provides a releasable retaining mechanism for maintaining retraction member 52 in its position as shown in FIGS. 1 and 2 against the force exerted on retraction member 52 by spring 82, tending to urge retraction member 52 rearwardly within passage 42.

Referring to FIGS. 1 and 2, a needle assembly 86 is located at the forward end of barrel 22. Needle assembly 86 includes a needle 88 defining a lumen, and a hub 90 to which needle 88 is mounted. In FIG. 1, needle 88 is shown enclosed by a conventional needle sheath 91. As shown in FIG. 2, hub 90 defines an internally threaded passage 92. Needle 88 extends forwardly from a flange 94, and an externally threaded hollow stud 96 extends rearwardly from flange 94. Stud 96 is threaded into internally threaded passage 92 of hub 90, to mount needle assembly 86 to hub 90.

Needle 88 is manually engaged with hub 90 just prior to use of syringe assembly 20 by threading stud 96 into threaded passage 92 of hub 90. This way, a user can stock several different sizes of needle 88, and select the appropriate needle size for the particular application.

Hub 90 includes a cavity 98 in communication with passage 92. A shoulder 100 defines a narrowed entryway into cavity 98. A tapered wall 102 extends rearwardly from shoulder 100, defining a rearwardly facing opening in hub 90. Tapered wall 102 terminates in a rearward annular end 104 (FIG. 2).

As a means for engaging needle assembly 86 with barrel 22, a sleeve 106 and a retainer member, shown generally at 108, are mounted to barrel end wall 30. Sleeve 106 defines a thickened forward portion 110 and a rearward portion 112. Rearward portion 112 defines an internal groove within which rib 32 on barrel end wall 30 is received, for mounting sleeve 106 to end wall 30 upon application of a push-on force. Forward portion 110 of sleeve 106 defines an internal groove 114 within which an O-ring 116 is seated. The inner periphery of O-ring 116 engages the outer surface of hub 90, for providing a fluid-tight seal to barrel internal cavity 27.

Sleeve 106 further defines an annular seat 118, which provides a transition between thickened forward portion 110 and rearward portion 112. Seat 118 faces end 34 of barrel end wall 30.

Retainer member 108 consists of a base 120 and a series of resilient fingers 122 extending rearwardly from base 120. Base 120 is sandwiched between seat 118 and end 34 of barrel end wall 30, for fixing retainer member 108 in position relative to barrel 22 and sleeve 106. Each of fingers 122 defines a shoulder 124, which engages annular end 104 defined by hub 90. Each finger 122 further defines a ramped surface 126 located rearwardly of shoulder 124.

In operation, syringe 20 functions as follows. The user first removes sheath 91 to expose needle 88. Needle 88 is inserted into a patient, and liquid contained within barrel cavity 27 is ejected therefrom into the patient by movement of plunger 24 in a right-to-left direction toward hub 90. The liquid passes from barrel cavity 27 into hub cavity 98, through passage 92 and hollow stud 96 into the lumen of needle 88.

As plunger head 48 approaches the inner surface of barrel frustoconical wall 28, retraction member head 54 passes between ramped surfaces 126 of retainer member fingers 122 and tapered wall 102 defined by hub 90, until retraction member head 54 is disposed within hub cavity 98 as shown in FIG. 2. In this position, shoulder 60 defined by retraction member head 54 engages shoulder 100 defined by hub cavity 98, so as to engage retraction member 52 with hub 90, and thereby with needle assembly 86. As head 54 is forced into hub cavity 98, angled actuator surface 62 of retraction member 52 engages ramped surfaces 126 defined by retainer member fingers 122, to deflect fingers 122 outwardly to their position as shown in FIG. 2. When fingers 122 are in this position, engagement between hub 90 and barrel 22 is released. Needle assembly 86 is thus subjected to the rearward bias exerted by spring 82, and is retained in position by retaining ring 84. With plunger 24 in its FIG. 2 position, substantially the entire amount of liquid contained within barrel cavity 27 is ejected therefrom through needle 88. Upon final forward movement of plunger 24 to its position of FIG. 3, retaining ring 84 is inverted and forced over ring 66 mounted to retraction member 52, to release engagement between plunger 24 and retraction member 52. Once retaining ring 84 is moved to its FIG. 3 position, spring 82 functions to withdraw retraction member 52 and needle assembly 86 rearwardly into passage 42, to its position as shown in FIG. 4. With needle assembly 86 in its FIG. 4 position, access to the tip of needle 88 is prevented, to avoid inadvertent contact with needle 88 after use of syringe 20. Syringe 20 is thus permanently disabled, and needle assembly 86 cannot thereafter be returned to its FIG. 1 position for reuse.

An alternative form of the invention is illustrated in FIGS. 5-7. As shown in FIGS. 5-7, a syringe assembly 130 consists of a barrel 132 and a plunger assembly. The plunger assembly, including retraction member 52, is identical to that disclosed in the embodiment of FIGS. 1-4, and accordingly like reference characters will be used where possible to facilitate clarity.

In the embodiment of FIGS. 5-7, barrel 132 includes a frustoconical wall 134, and a cylindrical end wall 136. An O-ring 138 is seated within an internal groove formed in end wall 136. A manually operable actuator member 140 is engaged with end wall 136. Referring to FIGS. 6 and 7, actuator member 140 includes an engagement surface 142 and a transverse plate portion 144. An opening is formed in plate portion 144. The opening includes a circular upper portion 146 and a slot-like lower portion 148. Actuator member 140 is mounted within a slot 150 formed in barrel end wall 136, between a retaining position as shown in FIGS. 5-7 in which slot-like lower opening portion 148 is aligned with the longitudinal axis of end wall 136, and a release position in which circular upper opening portion 146 is aligned with the longitudinal axis of barrel end wall 136. Actuator member 140 is movable between its retaining and release positions in response to application of a transverse force exerted on actuator member engagement surface 142 in a direction perpendicular to the longitudinal axis of barrel end wall 136.

In the embodiment of FIGS. 5-7, a needle assembly 152 consists of a needle 154 mounted to a hub 156 in the same manner described with respect to needle assembly 86 in the embodiment of FIGS. 1-4. Referring to FIG. 7, needle assembly hub 156 includes a pair of slots 158, 160 which receive plate portion 144 of actuator member 140 adjacent slot-like lower opening portion 148, when actuator member 140 is in its retaining position. With this construction, downward movement of actuator member 140 to its release position moves the material of plate portion 144 out of engagement with slots 158, 160 in hub 156.

Figure 3:
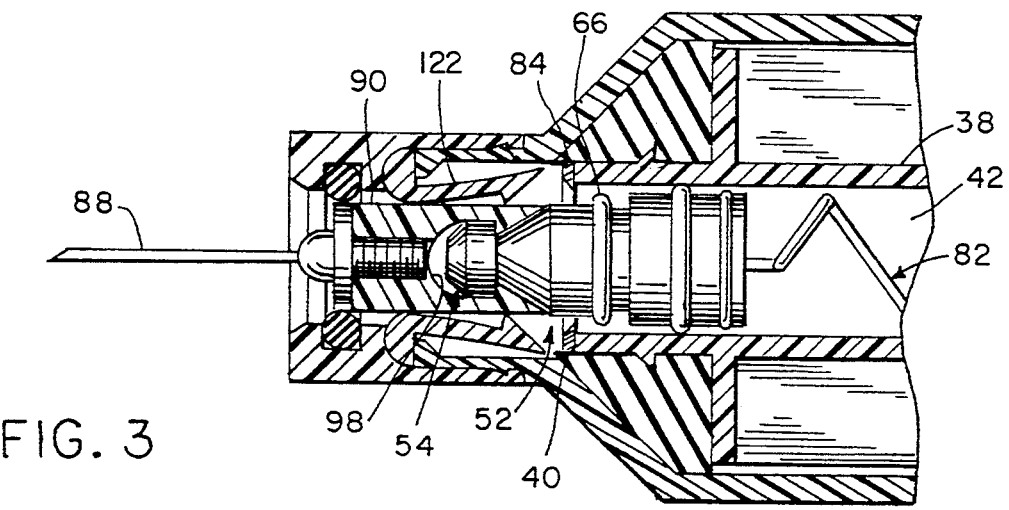
FIG. 3 is a view similar to FIG. 2, showing final movement of the plunger toward the first end of the barrel for releasing engagement between the retraction member and the plunger.
Figure 8:
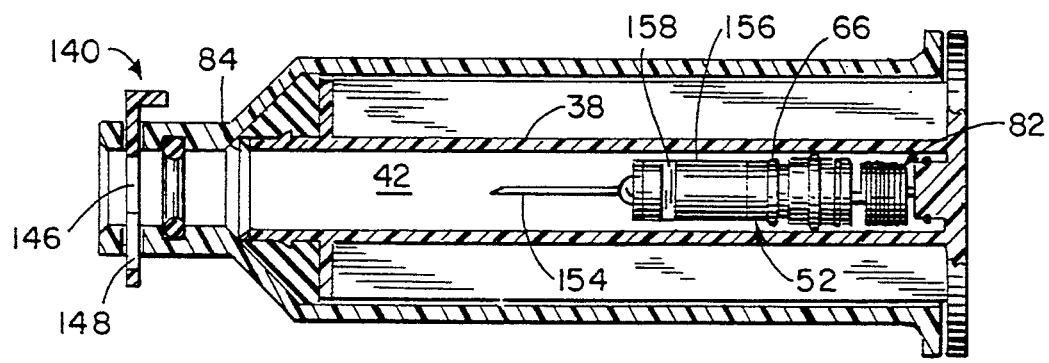
FIG. 8 is a view similar to FIG. 4, showing the actuator member moved to its release position for providing withdrawal of the needle assembly into the internal passageway defined by the plunger under the influence of the biasing means.

In operation, the embodiment of FIGS. 5-7 initially functions identically to the embodiment of FIGS. 1-4 as described previously. After retainer member head 54 is engaged within hub cavity 98, as shown in FIG. 6, the user continues forward movement of plunger 24 until a position as illustrated in FIG. 3 is attained, wherein retainer ring 84 is forced by end 40 of cylindrical wall 38 over ring 66, to release engagement of retraction member 52 with plunger 24. As before, this subjects retraction member 52 and hub 156 to the bias of spring 82, urging needle 154 rearwardly toward passage 42 defined by cylindrical wall 38. When it is desired to retract needle 154, the user manually engages his or her finger with actuator member engagement surface 142, and exerts a force thereon transverse to the longitudinal axis of barrel end wall 136, to move actuator member 140 to its release position in which the center of circular opening portion 146 is in alignment with the longitudinal axis of hub 156. Circular opening portion 146 is sized so as to release engagement between actuator member 140 and hub 156 when actuator member 140 is in its release position. This action releases engagement between barrel 132 and hub 156, and spring 82 then functions to withdraw retraction member 52, hub 156 and needle 154 into passageway 42, as illustrated in FIG. 8. As in the embodiment of FIGS. 1-4, this functions to disarm and prevent subsequent use of syringe assembly 130.

Figure 9:
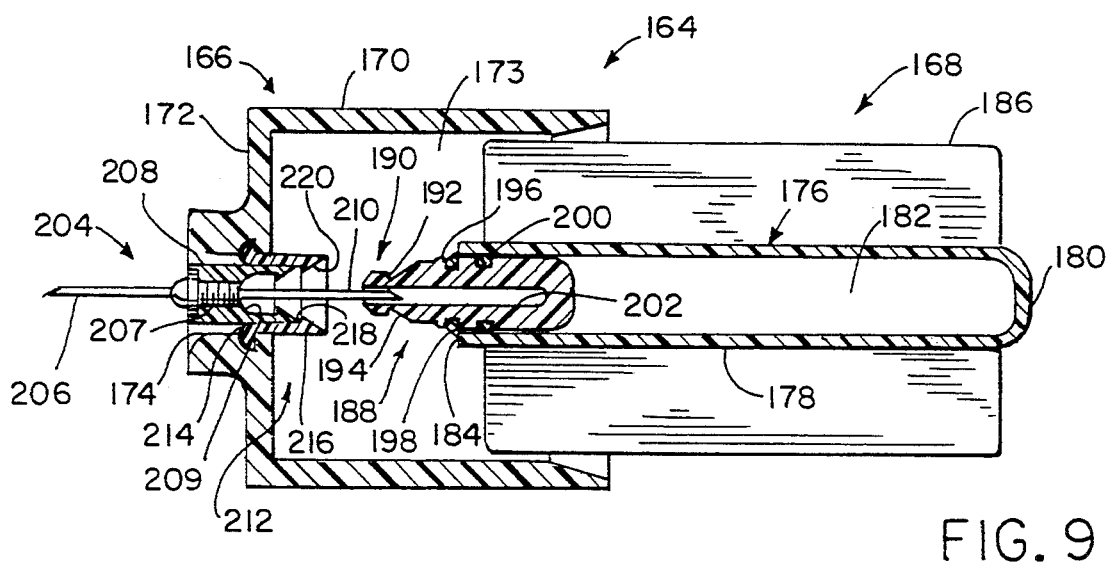
FIG. 9 is a longitudinal section view similar to FIGS. 1 and 5, showing another embodiment of an automatically retractable assembly constructed according to the invention.

FIG. 9 illustrates an embodiment of the invention incorporating a needle retraction mechanism similar to that of FIGS. 1-4 into a blood collection system. In this embodiment, a retractable needle blood collection system 164 includes a barrel-like cylindrical body 166 and a needle retrieving plunger assembly 168. Body 166 includes a side wall 170 and an end wall 172, which define an internal cavity 173. A central nipple is formed in end wall 172, defining a passage 174.

Plunger assembly 168 includes a central tube 176 having a side wall 178 and an end wall 180, and defining an internal passage 182. Side wall 178 terminates opposite end wall 180 in an annular end 184. A plunger outer body portion 186 is provided outwardly of central tube 176.

A retraction member 188 is mounted at the end of central tube 176 adjacent its annular end 184. Retraction member 188 includes a head 190 constructed similarly to head 54 in the embodiments of FIGS. 1-7, and defining a shoulder 192. Head 190 further defines a tapered actuator surface 194 and a rib 196, against which a retaining ring 198 is placed. Retaining ring 198 is engaged between rib 196 and annular end 184 of plunger tube side wall 178, for retaining retraction member 188 in its position as shown in FIG. 9. Retraction member 188 further includes a groove within which an O-ring 200 is seated, for providing a fluid-tight seal between central tube passage 182 and internal cavity 173 defined by syringe body 166. A central passage 202 is formed in retraction member 188, opening onto the forward surface of head 190 and extending rearwardly therefrom.

Passage 182 in plunger central tube 176 is evacuated. The vacuum behind retraction member 188 functions to bias retraction member 188 toward central tube end wall 180. Engagement of retaining ring 198 between central tube end 184 and rib 196 functions to retain retraction member 188 in its position as shown in FIG. 9 against the bias provided by the vacuum within passage 182.

A needle assembly 204 is located within passage 74 defined by the nipple formed in body end wall 172. Needle assembly 204 is similar in construction to needle assemblies 86, 152 illustrated in the embodiments of FIGS. 1-7, including a needle 206, a threaded stud 207, and a hub 208 constructed identically to hubs 90, 156 in the embodiments of FIGS. 1-4 and 5-7, respectively. Hub 208 includes an internally threaded passage and a hub cavity 209. A piercing needle 210 extends rearwardly from stud 207 to establish communication between body internal cavity 173 and the lumen of needle 206. In a manner as is known, piercing needle 210 is employed to pierce the membrane of an evacuated tube (not shown) for withdrawing blood from a patient after needle 206 is inserted into a blood vessel.

A retainer member 212 is engaged with hub 208 in the same manner as retainer member 108 in the embodiment of FIGS. 1–4, for retaining needle assembly 204 in its FIG. 9 position. Retainer member 212 includes an annular base 214 received within an internal groove formed in passage 174, and a series of rearwardly extending fingers 216. Each finger 216 defines a shoulder 218 and a tapered engagement surface 220.

In operation, the embodiment of FIG. 9 functions as follows. Needle 206 is first engaged with body 166 by threading stud 207 into the internally threaded passage of hub 208. The user then inserts needle 206 into a blood vessel, and withdraws blood from the patient by inserting an evacuated tube (not shown) into body cavity 173 such that piercing needle 210 punctures the membrane of the evacuated tube, in a manner as is known. The vacuum within the evacuated tube draws blood through needle 206 and piercing needle 210 into the evacuated tube. When the user has completed drawing blood from the patient, needle retrieving plunger assembly 168 is then inserted into body cavity 173 in a right-to-left direction. During such movement of plunger assembly 168, piercing needle 210 is received within internal passage 202 of retraction member 188. As right-to-left movement of plunger assembly 168 continues, head 190 of retraction member 188 is engaged within hub cavity 209, in a manner similar to that shown in FIGS. 2, 3 and 6 in the embodiments of FIGS. 1–4 and 5–7, respectively. When retraction member 188 is in this position, its actuator surface 194 engages tapered surfaces 220 of fingers 216, to flex fingers 216 outwardly in a manner similar to that shown and described with respect to fingers 122 in FIGS. 2 and 3. With fingers 216 in this position, engagement between hub 208 and body 164 is released. Additional right-to-left movement of plunger 168 results in end 184 of central tube side wall 178 forcing retaining ring 198 over rib 196 of retraction member 188, to release engagement between retraction member 188 and plunger 168. When this occurs, the vacuum within passage 182 functions to draw retraction member 188 and needle assembly 204 into passage 182, to simultaneously withdraw needle 206 from the patient's blood vessel and to disarm blood collection system 164. Passage 182 has a length sufficient to harbor needle 206 therewithin, to disarm syringe system 164 and to prevent subsequent reuse. Passage 202 in retraction member 188 is provided with a length sufficient to receive the entire length of piercing needle 210 during forward movement of plunger 168 relative to body 166.

Figure 10:
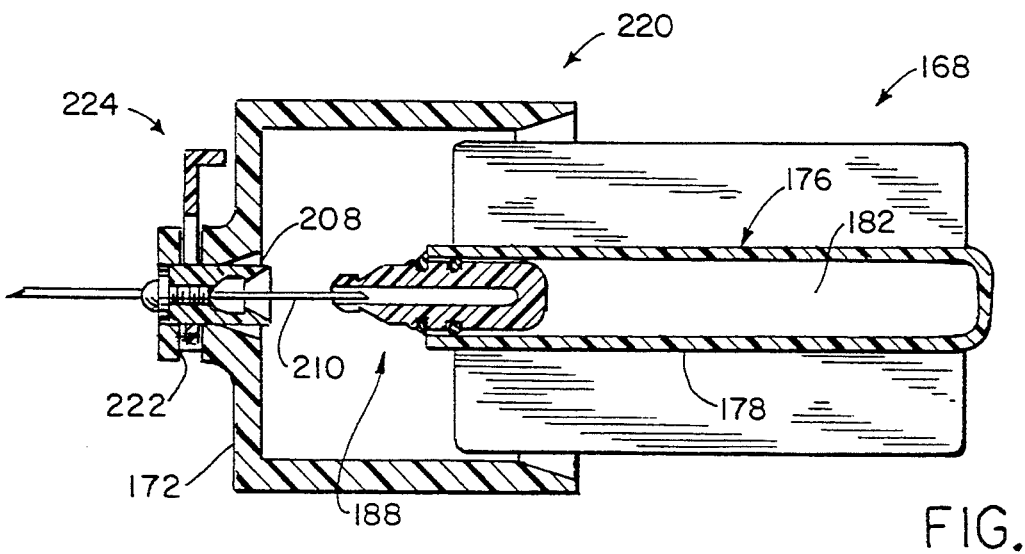
FIG. 10 is a longitudinal section view similar to FIG. 9, showing another embodiment of a manually operable retractable assembly constructed according to the invention.

FIG. 10 illustrates a manually actuated retractable needle blood collection system 220 somewhat similar to blood collection system 164 illustrated in FIG. 9. The FIG. 10 embodiment includes a plunger assembly and retraction member identical to that shown and described in the embodiment of FIG. 9, and like reference characters will be used to facilitate clarity. In addition, FIG. 10 includes a body, end wall and needle assembly substantially similar to that shown and described with respect to the embodiment of FIG. 9, and again like reference characters will be used to facilitate clarity.

In the FIG. 10 embodiment, the nipple formed in body end wall 172 defines a slot 222 within which a manually operated actuator member 224 is received. Actuator member 224 is constructed identically to actuator member 140 in the embodiment of FIGS. 5–7. Hub 208 is provided with slots within which the material of actuator member 224 is disposed when actuator member 224 is in its retaining position as shown in FIG. 10, for engaging hub 208 with body 166 of syringe system 220. As in the embodiment of FIGS. 5–7, manual downward movement of actuator member 224 after use of blood collection system 220 disengages actuator member 224 from hub 208, thus providing retraction of retraction member 188 and needle assembly 204 into central tube passage 182, in a manner similar to that described with respect to the embodiment of FIG. 9.

Yet another alternative form of the invention is illustrated in FIGS. 11–17. In this embodiment, a syringe assembly 230 generally includes a barrel 232 and a plunger 234. Barrel 232 includes a cylindrical side wall 236 defining an internal cavity 238, and a frustoconical end wall 240 which defines a tapered central passage 242 extending between cavity 238 and the exterior of end wall 240.

A sleeve, shown generally at 244, is received within passage 242 for mounting sleeve 244 to barrel 232. Sleeve 244 includes an end tip 246 defined by a tapered side wall 248 and an end wall 250, which defines a central opening 252 communicating between the exterior of tip 246 and an internal passage 254 defined by side wall 248 in combination with end wall 250.

Sleeve 244 further includes a tubular portion 256 extending rearwardly from tip 246, with a shoulder 258 defined therebetween. Tubular portion 256 includes a side wall 260 having a circular cross-section and a continuous linear outer surface. The inner surface of side wall 260 includes a pair of circumferential shoulders 262, 264, which define steps in the passage, shown at 266, defined by tubular portion 256. Tip passage 254 and tubular portion passage 266 are in communication with each other.

The upper portion of tubular portion wall 260 is provided with a channel 268, the purpose of which will later be explained.

A series of transverse passages, two of which are shown at 270, 272, extend through tubular portion side wall 260 adjacent shoulder 258 and the inner surface defined by barrel end wall 240. With this arrangement, the passages, such as 270, 272, establish communication between barrel cavity 238 and passage 266 defined by sleeve tubular portion 256.

A hub member 272 is mounted within sleeve 244. Hub member 272 includes a forward needle-receiving portion having a series of resilient fingers 274, each of which terminates in an inwardly extending hook 276. Fingers 274 define a tapered recess 278, which is adapted to receive a needle head 280 having a correspondingly tapered external surface 282. Needle head 280 further defines an annular shoulder 284. A needle 286 defining a lumen 288 is received within an internal passage defined by needle head 280, which further defines a passage 290 establishing communication between needle lumen 288 and the end of needle head 280.

With this construction, the needle assembly, consisting of needle head 280 and 286, is engaged with hub member 272 just prior to use of syringe assembly 230. The needle assembly is selected from a variety of similarly constructed needle assemblies having differently sized needles, and the operator selects the appropriately sized needle for the application in which syringe assembly 230 is to be used. The operator inserts needle head 280 through opening 252 in end wall 250 of sleeve tip 246, to engage needle head external surface 282 with hooks 276 and fingers 274 of hub member 272. Continued insertion of needle head 280 results in fingers 274 deflecting outwardly until needle head 280 is in its FIG. 11 position, in which shoulder 284 has passed hooks 276. With needle head 280 in this position, fingers 274 deflect back inwardly toward each other, to engage hooks 276 with shoulder 284 to positively retain needle head 282 within hub member recess 278 and to prevent subsequent removal of the needle assembly. Alternatively, of course, it is understood that a threaded connection, similar to that disclosed in FIGS. 1–10, could be employed to secure the needle to hub member 272.

Hub member 272 further includes a series of passages, such as shown at 292, 294, which are aligned with the passages, such as 270, 272, formed in sleeve side wall 260, to establish communication between barrel cavity 238 and a central passage 296 formed in hub member 272. Central passage 296 in turn is in communication with passage 290 formed in needle head 280. In this manner, when hub member 272 is in its FIG. 11 position, communication is established between barrel cavity 238 and needle lumen 288.

O-rings, such as shown at 298, 300, are fitted within circumferential grooves formed in hub member 272. O-rings 298, 300 provide a fluid-tight seal between hub member 272 and sleeve 244 on either side of the passages, such as 292, 294, in hub member 272, and the passages, such as 270, 272, in sleeve side wall 260.

The rearward end of hub member 272 is provided with an outwardly extending annular lip 302. A spring 304 is positioned between lip 302 and shoulder 262 formed in the inner surface of sleeve side wall 260.

Figure 11:
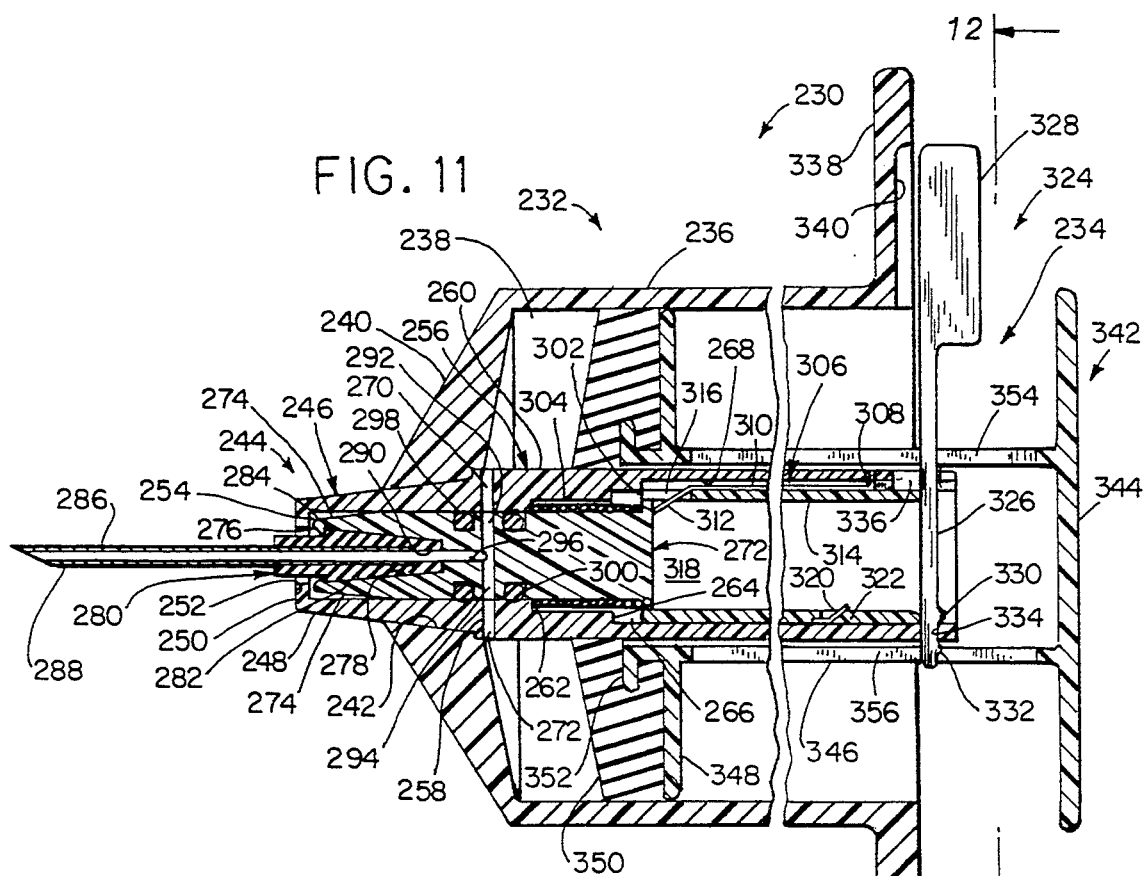
FIG. 11 is a longitudinal cross-sectional view of a syringe incorporating another embodiment of the needle retraction apparatus and method of the invention, showing the needle assembly and hub member retained in their extended position.
Figure 13:
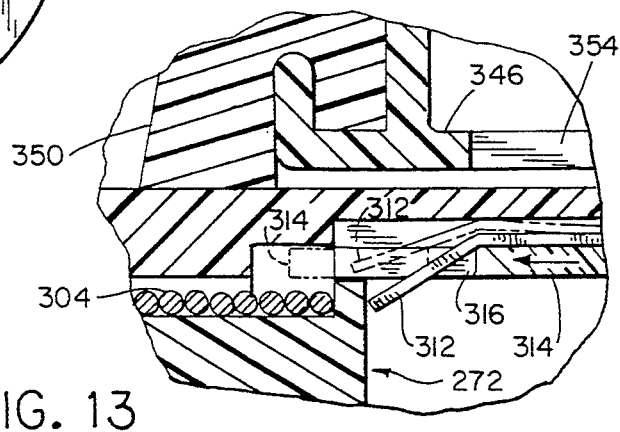
FIG. 13 is an enlarged partial section view of a portion of the syringe of FIG. 11, showing the releasable retainer mechanism for maintaining the hub member in a position in which the needle is in its armed condition.

A releasable retainer mechanism is interposed between sleeve 244 and hub member 272 for releasably retaining hub member 272 in its FIG. 11 position. Referring to FIGS. 11 and 13, the releasable retainer mechanism includes a retainer member 306 having a transverse rear end section 308 received within an opening formed in sleeve side wall 260 for maintaining retainer member 306 in a fixed longitudinal position relative to sleeve side wall 260. Retainer member 306 further includes a longitudinally extending middle section 310, and an inwardly bent forward end section 312, the end of which engages the rearward surface of hub member 272. Longitudinal middle section 310 of retainer member 306 is received within channel 268 formed in the internal surface of sleeve side wall 260.

An actuator tube 314 is mounted for longitudinal movement within the internal passage 266 defined by sleeve side wall 260. Actuator tube 314 includes a slot 316 within which the forward end section of retainer member 306 is received. Actuator tube 314 defines an internal passage 318, and the rearward end of hub member 272 is engaged within the forward end of passage 318. Actuator tube 314 further includes a resilient one-way lock member 320, the outer end of which extends into passage 318 through an opening 322 formed in the side wall of actuator tube 314.

Figure 12:
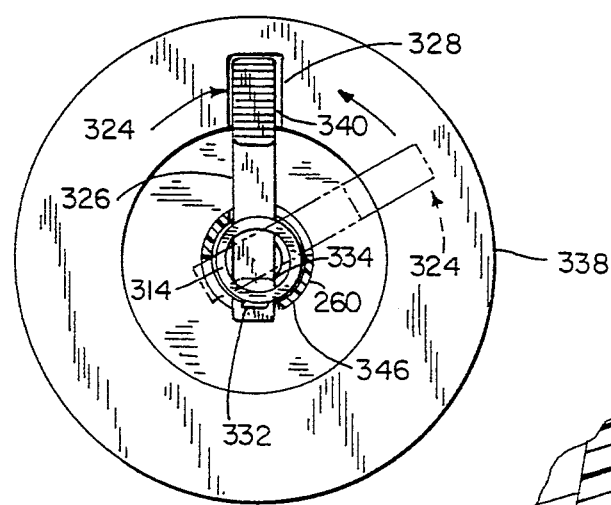
FIG. 12 is an end elevation view, reference being made to line 12—12 of FIG. 11, showing the manually operated actuator mechanism for the syringe of FIG. 11.

A manually operable triggering lever 324 is pivotably mounted to the rearward end of sleeve 244 for selectively moving actuator tube 314 between its positions as shown in FIGS. 11 and 12, in a manner to be explained. Triggering lever 324 includes a mounting stem 326 and a finger-actuable outer trigger portion 328. A pair of spaced protrusions 330, 332 are provided at the end of mounting stem 326 opposite trigger portion 328, and are engaged with the inner and outer surfaces, respectively, of sleeve side wall 260, with the portion of mounting stem 326 located therebetween being disposed within an opening 334 formed in sleeve side wall 260. Between protrusion 330 and trigger portion 328, mounting stem 326 extends through a slot 336 formed in sleeve side wall 260 opposite opening 334.

Referring to FIGS. 11 and 12, lever 324 is pivotable relative to the longitudinal axis of sleeve 244 between an inoperative position, shown in phantom in FIG. 12, and an operative position shown in solid lines in FIG. 12. Opening 332 and slot 336 are configured so as to allow such pivoting movement of lever 324 between its inoperative and operative positions.

As shown in FIGS. 11 and 12, syringe barrel 232 terminates at its outer end in a flange 338. Flange 338 includes a depression 340 disposed below trigger portion 328 of lever 324 when lever 324 is in its operative position.

Figure 14:
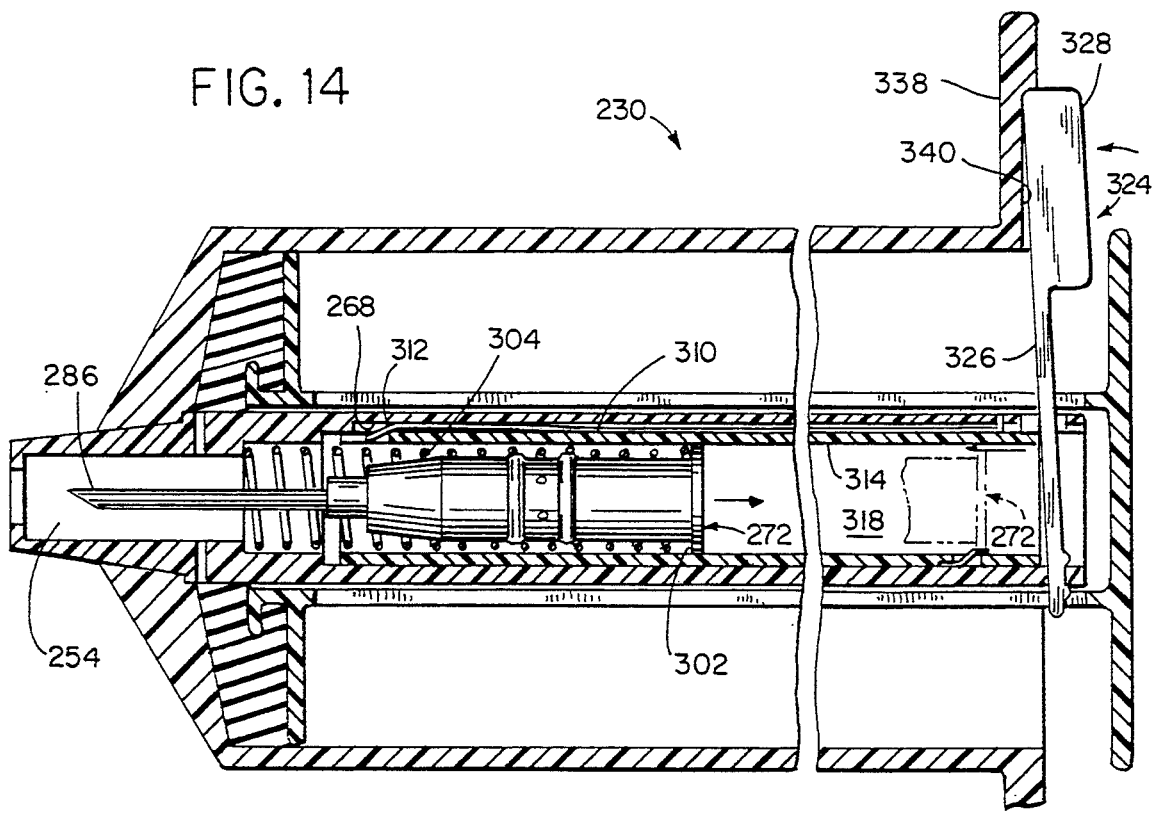
FIG. 14 is a longitudinal cross-sectional view similar to FIG. 11, showing actuation of the manually operated actuator mechanism for moving the releasable retainer mechanism to its release position to withdraw the hub member, and thereby the needle assembly, into the sleeve.
Figure 15:
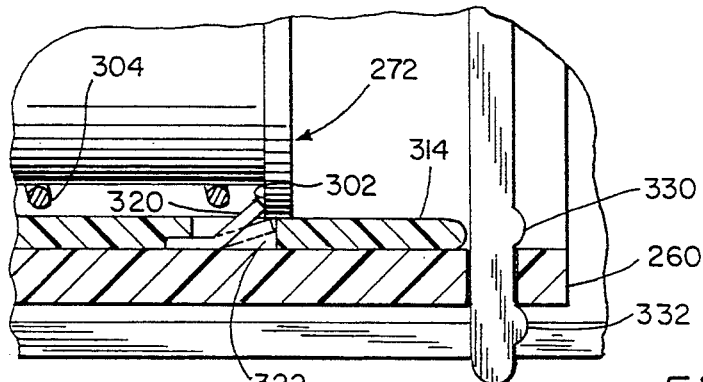
FIG. 15 is an enlarged partial sectional view illustrating the one-way retainer mechanism for retaining the hub member in position at the second end of the sleeve once the syringe assembly has been disarmed.

Lever 324 is pivotable between its positions shown in FIGS. 11 and 14 about a pivot point defined between protrusions 330, 332 at the point of connection between mounting stem 326 and sleeve side wall 260. When lever 324 is in any position other than in its operative position as shown in FIG. 12, lever 324 cannot be depressed due to engagement of the forward surface of trigger portion 328 with the rearward surface of barrel flange 338. However, when lever 324 is moved to its operative position as shown in FIG. 12, trigger portion 328 is movable into depression 340 so as to provide pivoting movement of lever 324 to its FIG. 14 position.

As shown in FIG. 11, a plunger assembly 342 is slidably mounted within barrel cavity 238. Plunger assembly 342 includes a plunger having a thumb plate 344, a tubular side wall 346, and an inner end ring 348. A resilient plunger head 350 is mounted to the forward end of the plunger, and is retained in place by a ring 352 located forwardly of ring 348 and disposed within a mating annular recess formed in head 350. Plunger side wall 346 includes a pair of longitudinal slots 354, 356 through which mounting stem 326 of trigger member 324 extend, to allow plunger 342 to be moved longitudinally relative to barrel 232 without interference from stem 326.

Referring to FIGS. 11–15, syringe assembly 230 functions as follows. First, as described previously, the operator selects an appropriate size of needle 286, having an associated head 280, and mounts the needle assembly to the forward end of hub member 272 as described previously. A sheath or the like is placed over needle 286 while the needle assembly is being installed, and is subsequently removed to expose the sharpened end of the needle. With lever 324 in its inoperative phantom line position of FIG. 12, the operator inserts the needle in a desired location into the patient, and depresses plunger assembly 342 using thumb plate 344 to eject the fluid contained within barrel cavity 238 into the patient through needle lumen 288. When as much of the fluid as desired has been injected into the patient, the user moves lever 324 to its operative solid line position as shown in FIG. 12, to position trigger portion 328 over depression 340. The user then uses his or her thumb or finger to engage trigger portion 328 and depress lever 324, in a manner as shown in FIG. 14, into depression 340. Alternatively, thumb plate 344 and lever 324 may be constructed such that, when plunger assembly 342 is in its full-forward position, thumb plate 344 engages trigger portion 328 to depress lever 344. This causes pivoting movement of lever 324, which results in axial forward movement of actuator tube 314 relative to sleeve 244. The forward end of actuator tube 314 engages the inwardly bent forward section 312 of retainer member 306, to move the end of retainer member 306 out of engagement with hub member 272. This movement of retainer member 306 to its release position results in spring 304 propelling hub member 272 rearwardly within passage 318 defined by actuator tube 314, to thereby withdraw needle 286 and its sharpened tip into passage 266 defined by sleeve 244. This disarmed condition of syringe assembly 230 is illustrated in FIG. 14. Spring 304 continues to propel hub member 272 rearwardly such that hub member lip 304 passes over one-way lock member 320, which flexes outwardly to allow passage of hub member lip 302 thereover. Lock member 320 then returns to its original position due to its resiliency, and engages the forward surface of lip 302 to subsequently prevent hub member 272 from moving forwardly within actuator tube passage 318. This prevents subsequent reuse of syringe assembly 232.

The above steps in withdrawing needle 286 can be undertaken either before or after needle 286 has been withdrawn from the patient.

As can be appreciated, syringe assembly 230 can be operated to withdraw needle 286 whether or not all of the fluid contained within barrel cavity 238 has been ejected by forward movement of plunger assembly 342.

Figure 16:
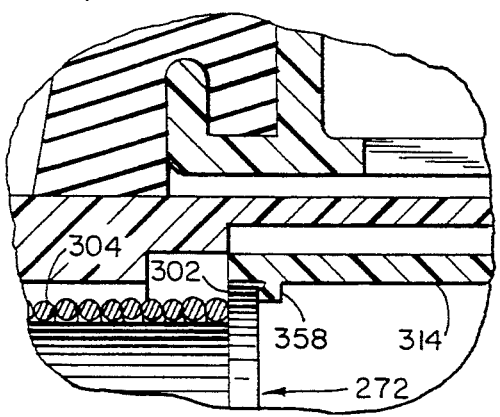
FIG. 16 is an enlarged partial sectional view similar to FIG. 13, showing an alternative embodiment for the releasable retainer mechanism for retaining the hub member in position adjacent the first end of the sleeve.
Figure 17:
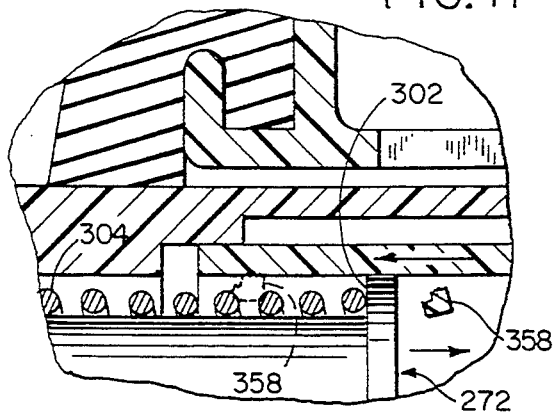
FIG. 17 is a view similar to FIG. 16, showing the manner in which the releasable retainer mechanism of FIG. 16 is moved to its release position to allow the hub member to be withdrawn into the sleeve.

FIGS. 16 and 17 illustrate an alternative retainer arrangement for releasably retaining hub member 272 in its forward position. Like reference characters will be used where possible to facilitate clarity. As shown in FIG. 16, a frangible retainer element 358 is formed integrally with actuator tube 314, extending inwardly from the inner wall defined by actuator tube 314. Retainer element 358 has sufficient strength to maintain hub member 272 in its forward position during use of syringe assembly 230 while plunger assembly 342 is operated to eject fluid from barrel cavity 238. When lever 324 is moved to its FIG. 12 solid line position and depressed as shown in FIG. 14, actuator tube 314 again moves forwardly within sleeve passage 266, and such forward movement of actuator tube 314 functions to break frangible retainer element 358 away from actuator tube 314. This releases engagement between hub 272 and sleeve 244, resulting in spring 304 propelling hub member 272 rearwardly within passage 318 defined by actuator tube 314. Frangible retainer element 358 is used in place of retainer member 306 (FIGS. 11-14) to releasably maintain hub member 272 in its forward position. Alternatively, a frangible tab or ring element could be formed integrally with lip 302 of hub member 272 in place of frangible element 358.

While the invention as shown in FIGS. 11-17 has been described as a syringe assembly, it is understood that the illustrated assembly could also be used as a device for withdrawing a body fluid from a patient, with actuation of the mechanism to withdraw needle 286 occurring after a desired amount of fluid has been withdrawn from the patient.

Various alternatives and embodiments are contemplated as being within the scope of the following claims particularly pointing out and distinctly claiming the subject matter regarded as the invention.

We claim:
1. A medical assembly, comprising:
a barrel having an internal cavity and defining a first end and a second end;
a plunger assembly adapted for longitudinal sliding movement within the barrel cavity;
structure defining a longitudinal passage disposed within the barrel cavity;
a hub member mounted to the barrel adjacent its first end and receivable into the longitudinal passage;
retraction means for retracting the hub member into the passage; and
a needle assembly separate from the hub member and selectively mountable to the hub member from the exterior of the barrel, the needle assembly including a needle head and a needle mounted thereto and extending forwardly therefrom, the needle terminating in a sharpened end, wherein the retraction means functions to retract the hub member into the internal passage to enclose the sharpened end of the needle when the needle assembly is mounted to the hub member.

2. The assembly of claim 1, wherein the needle assembly is mountable to the hub member by means of a series of external threads provided on the needle head engageable with a series of internal threads provided within a passage formed in the hub member.

3. The assembly of claim 2, wherein the hub member defines a forward end, and further comprising a flange member provided on the needle head engageable with the forward end of the hub member.

4. The assembly of claim 1, wherein the needle assembly is mountable to the hub member by means of mating structure provided on the hub member and on the needle head for providing push-on engagement of the needle assembly with the hub member.

5. A medical assembly, comprising:
a barrel having an internal cavity and defining a first end and a second end;
a plunger assembly adapted for longitudinal sliding movement within the barrel cavity;
structure defining a longitudinal passage disposed within the barrel cavity;
a hub member mounted to the barrel adjacent its first end;
means for retracting the hub member into the passage; and
a needle assembly selectively mountable to the hub member from the exterior of the barrel, the needle assembly including a needle head and a needle mounted thereto and extending forwardly therefrom, the needle terminating in a sharpened end, wherein retraction of the hub member into the internal passage functions to enclose the sharpened end of the needle, wherein the needle assembly is mountable to the hub member by means of mating structure provided on the hub member and on the needle head for providing push-on engagement of the needle assembly with the hub member, wherein the mating structure comprises a tapered forwardly facing passageway formed in the hub member defined by a series of outwardly deformable fingers, wherein each finger defines an outer end, and wherein an inwardly extending hook is formed at the outer end of each finger, and a mating tapered external surface provided on the needle head engageable within the tapered recess provided in the hub member, the needle head further defining a shoulder, wherein push-on engagement of the needle head tapered surface within the tapered recess deflects the fingers outwardly until passage of the shoulder past the hooks, wherein the hooks return to their undeformed condition to engage the shoulder and to retain the tapered needle head within the tapered recess.

6. The assembly of claim 1, wherein the hub member includes a passage in communication with the barrel cavity, and wherein the needle head includes a passage in communication with the hub member passage, whereby communication is established through the hub member and needle head passages between the barrel cavity and the needle.

7. The assembly of claim 1, wherein the structure defining a longitudinal passage comprises a tubular structure fixedly interconnected with the barrel.

8. The assembly of claim 7, wherein the barrel first end includes a passage, and wherein the tubular structure comprises a sleeve having a first end portion extending through the passage in the barrel first end and a second end portion into which the needle assembly and hub member are retracted by the retraction means, and wherein the hub member is slidably mounted within the sleeve toward its first end portion.

9. The assembly of claim 8, wherein the first end portion of the sleeve is open and wherein the needle assembly is engageable with the hub member therethrough.

10. The assembly of claim 7, wherein the tubular structure defines a first end located adjacent the barrel first end, and wherein the hub member is slidably mounted within the tubular structure toward its first end, and wherein the retraction means includes a spring interposed between the hub member and the tubular structure for biasing the hub member toward a second end of the tubular structure spaced from the first end, and a releasable retainer assembly selectively operable by a user for releasably retaining the hub member toward the first end of the tubular structure against the force of the spring and for releasing engagement with the hub member upon actuation by a user to move the hub member toward the second end of the tubular structure, under the influence of the spring, to enclose the hub member and needle assembly within the tubular structure.

11. The assembly of claim 1, wherein the needle assembly is selectively mountable to and disengageable from the hub member.

12. A medical assembly, comprising:
a barrel having an internal cavity and defining a first end and second end, the barrel extending along a longitudinal axis;
a plunger assembly adapted for longitudinal sliding movement within the barrel cavity;
a sleeve mounted to the barrel, the sleeve defining a forward end and a rearward end and an internal passage extending therebetween, wherein the sleeve extends through the plunger assembly and wherein the plunger assembly is longitudinally movable relative to the sleeve;
a hub member mounted within the sleeve in a first position toward the forward end of the sleeve;
a needle mounted to the hub member, the needle defining a lumen, wherein the hub member includes passage means establishing communication between the needle lumen and the barrel cavity;
bias means for urging the hub member toward the rearward end of the sleeve;
a releasable retainer mechanism for retaining the hub member in its first position against the force of the bias means and movable to a release position for disengaging the hub member; and
a manually operable trigger member for selectively moving the releasable retainer mechanism to its release position, wherein engagement between the sleeve and the hub member is released and the bias means functions to propel the hub member, and thereby the needle, toward the rearward end of the sleeve to withdraw the needle into the internal passage defined by the sleeve;
wherein the needle assembly includes a needle and a needle head, wherein the needle head is selectively engageable with the hub member.

13. A medical assembly, comprising:
a barrel having an internal cavity and defining a first end and second end, the barrel extending along a longitudinal axis;
a plunger assembly adapted for longitudinal sliding movement within the barrel cavity;
a sleeve mounted to the barrel, the sleeve defining a forward end and a rearward end and an internal passage extending therebetween, wherein the sleeve extends through the plunger assembly and wherein the plunger assembly is longitudinally movable relative to the sleeve;
a hub member mounted within the sleeve in a first position toward the forward end of the sleeve;
a needle mounted to the hub member, the needle defining a lumen, wherein the hub member includes passage means establishing communication between the needle lumen and the barrel cavity;
bias means for urging the hub member toward the rearward end of the sleeve;
a releasable retainer mechanism for retaining the hub member in its first position against the force of the bias means and movable to a release position for disengaging the hub member; and
a trigger arrangement for selectively moving the releasable retainer mechanism to its release position, including a trigger member located toward the rearward end of the barrel, and a movable actuator member disposed within the sleeve for moving the releasable retainer mechanism to its release position in response to operation of the trigger member by the operator, wherein engagement between the sleeve and the hub member is released and the bias means functions to propel the hub member, and thereby the needle, toward the rearward end of the sleeve to withdraw the needle into the internal passage defined by the sleeve.

14. The assembly of claim 13, wherein the barrel includes a flange at its rearward end, and wherein the trigger member is pivotably mounted to the sleeve rearwardly of the flange.

15. The assembly of claim 14, wherein the flange includes a depression for receiving the trigger member to provide movement of the actuator member within the sleeve, and wherein the trigger is movable to an inoperative position out of alignment with the recess for preventing pivoting movement of the trigger member and movement of the actuator member.

16. The assembly of claim 15, wherein the actuator member comprises an actuator tube slidably mounted within the sleeve.

17. The assembly of claim 16, wherein the releasable retainer mechanism includes a retainer member mounted to the sleeve and defining a forward end engageable with the hub member for retaining the hub member in its forward position against the force of the bias means, and wherein forward movement of the actuator member in response to operation of the trigger member results in movement of the retainer member out of engagement with the hub member.

18. The assembly of claim 16, wherein the releasable retainer mechanism comprises a frangible retainer element provided on the actuator tube, wherein forward movement of the actuator tube in response to operation of the trigger member functions to break the frangible retainer member upon forward movement of the actuator tube in response to operation of the trigger member, to release engagement with the hub member and to provide retraction of the hub member into the actuator tube passage.

* * * * *